(12) United States Patent
Siedenburg

(10) Patent No.: US 8,311,309 B2
(45) Date of Patent: Nov. 13, 2012

(54) METHOD FOR IMPROVING THE ABILITY TO RECOGNIZE MATERIALS IN AN X-RAY INSPECTION SYSTEM, AND X-RAY INSPECTION SYSTEM

(75) Inventor: Uwe Siedenburg, Essenheim (DE)

(73) Assignee: Smiths Heimann GmbH, Wiesbaden (DE)

( * ) Notice: Subject to any disclaimer, the term of this patent is extended or adjusted under 35 U.S.C. 154(b) by 334 days.

(21) Appl. No.: 12/716,848

(22) Filed: Mar. 3, 2010

(65) Prior Publication Data
US 2010/0158384 A1 Jun. 24, 2010

Related U.S. Application Data

(63) Continuation of application No. PCT/EP2008/006344, filed on Aug. 1, 2008.

(30) Foreign Application Priority Data

Sep. 5, 2007 (DE) .......................... 10 2007 042 144

(51) Int. Cl.
G06K 9/00 (2006.01)
(52) U.S. Cl. .......................... 382/132; 382/131; 382/190
(58) Field of Classification Search .............. 250/361 R; 378/5, 51, 98, 98.8, 156, 19; 382/131, 132, 382/190
See application file for complete search history.

(56) References Cited

U.S. PATENT DOCUMENTS

| | | | |
|---|---|---|---|
| 5,081,659 A | | 1/1992 | Dobbbins |
| 5,481,584 A | | 1/1996 | Tang et al. |
| 6,052,433 A | * | 4/2000 | Chao .......................... 378/98.9 |
| 6,453,012 B2 | * | 9/2002 | Herbert .......................... 378/158 |
| 6,856,669 B2 | * | 2/2005 | Francke et al. .................. 378/86 |
| 7,283,608 B2 | * | 10/2007 | Hoffman .......................... 378/19 |
| 7,573,035 B2 | * | 8/2009 | Levene et al. .............. 250/361 R |
| 7,696,481 B2 | * | 4/2010 | Tkaczyk .................. 250/363.02 |
| 2002/0168046 A1 | * | 11/2002 | Hansen .......................... 378/51 |
| 2003/0118151 A1 | * | 6/2003 | Menhardt ........................ 378/62 |
| 2004/0234031 A1 | * | 11/2004 | Francke et al. ................. 378/98 |
| 2005/0145808 A1 | * | 7/2005 | Sawazumi .................... 250/584 |

(Continued)

OTHER PUBLICATIONS

Erich Krestel: "Dual energy imaging and hybrid subtraction", Imaging Systems for Medical Diagnostics, Jan. 1, 1990, pp. 375-377.

Primary Examiner — Gregory M Desire
(74) Attorney, Agent, or Firm — Muncy, Geissler, Olds & Lowe, PLLC

(57) ABSTRACT

A method for improving the ability to recognize materials in an X-ray inspection system is provided that includes the steps of recording at least two absorption X-ray images of an object to be examined at different energies, mathematically modeling the object by a number of layers assuming a particular material for each layer, wherein an absorption value describes the absorptivity of a layer, the number of layers is less than or equal to the number of X-ray images and at least one layer is assumed to be a material to be recognized during the inspection, decomposing the absorption value of each layer into a path-dependent factor and an energy-dependent factor, calculating the path-dependent factors for all layers from the absorption X-ray images using the absorption equation, calculating at least one synthetic image from the sum of all layers of the product of the absorption values and the weighting factors, evaluating the synthetic image.

14 Claims, 2 Drawing Sheets

U.S. PATENT DOCUMENTS

| | | | |
|---|---|---|---|
| 2006/0045236 A1* | 3/2006 | Hoffman | 378/19 |
| 2006/0269879 A1* | 11/2006 | Elian et al. | 430/394 |
| 2006/0280281 A1* | 12/2006 | Flohr et al. | 378/5 |
| 2010/0051820 A1* | 3/2010 | Okada | 250/370.09 |
| 2010/0158384 A1* | 6/2010 | Siedenburg | 382/190 |
| 2010/0195791 A1* | 8/2010 | Ishkhanov et al. | 378/57 |

* cited by examiner

METHOD FOR IMPROVING THE ABILITY TO RECOGNIZE MATERIALS IN AN X-RAY INSPECTION SYSTEM, AND X-RAY INSPECTION SYSTEM

This nonprovisional application is a continuation of International Application No. PCT/EP2008/006344, which was filed on Aug. 1, 2008, and which claims priority to German Patent Application No. DE 10 2007 042 144.5, which was filed in Germany on Sep. 5, 2007, and which are both herein incorporated by reference.

BACKGROUND OF THE INVENTION

1. Field of the Invention

The present invention relates to a method for improving the ability to recognize materials in an X-ray inspection system, and to an X-ray inspection system.

2. Description of the Background Art

It is known that in order to inspect objects, in particular pieces of luggage, in respect of suspicious contents, X-ray inspection equipment is used in which the objects to be inspected are irradiated by X-ray beams. For this, the X-ray inspection equipment has an X-ray source and detectors in which the intensities of the attenuated radiation are detected. Brightness values for a two-dimensional X-ray image displayed on a monitor are calculated from these intensities. Dangerous materials can be recognized in this X-ray image.

In contrast to computed tomography scanners in the medical sector, X-ray inspection equipment for security checks or nondestructive testing has fixed X-ray sources and detectors. Such X-ray inspection systems therefore only irradiate each spatial point of the inspection object in one direction. Hence, a three-dimensional reconstruction of the inspection object, required for determining the density, cannot be achieved. Therefore, materials situated behind one another in the beam path cannot be easily recognized.

SUMMARY OF THE INVENTION

It is therefore an object of the invention to provide a method that improves the ability to recognize materials in an X-ray inspection system.

In an embodiment of the invention, at least two absorption X-ray images of an object to be inspected are firstly recorded at different energies. Here, the energies are advantageously selected such that the intensity of the X-ray radiation transmitted through the object is reduced by different physical effects. It is preferable for two absorption X-ray images to be recorded at two different energies according to the known dual-energy method. Depending on the context, the term "X-ray image" refers to the measured X-ray intensities or the image calculated therefrom to be displayed on a monitor.

In general, the measured X-ray intensity is described by the absorption equation:

$$I(E) = \int_E I_0(E) \cdot e^{-\int_S \mu(E, r(s)) ds} dE \quad (1)$$

Here, $I_0$ refers to the energy-dependent intensity of the X-ray radiation, which would be incident on a detector if there were no material between the X-ray source and the detector, and $\mu$ describes the absorption coefficient depending on the spatial coordinate $r(s)$ within the object. S describes the path of the X-ray radiation through the object. Since X-ray inspection systems do not generally use mono-energetic X-ray radiation, there is integration in equation (1) over the energy spectrum of the X-ray radiation.

In a further method step, this is followed by the mathematical modeling of the object by a number of layers, assuming a particular material for each layer. Here, the number of layers is less than or equal to the number of X-ray images and at least one layer is assumed to be a material to be recognized during the inspection. Since the materials are assumed to be homogeneous, $\mu$ is constant within a layer and the integration over the path S is dispensed with. This results in the equation:

$$I(E) = \int_E I_0(E) \cdot e^{-\Sigma_M \mu_m(E) d_m} dE,$$

where $d_m$ is the thickness of the respective material, that is to say the extent of the layer in the direction of the X-ray radiation. M refers to the number of layers in the model. The absorptivity of the object is divided between the layers during the modeling; the absorptivity of a layer is described by an absorption value $\mu_m \cdot d_m$. The sum of the absorption values of the layers corresponds to the absorption value of the entire object:

$$\int_S \mu(E, r(s)) ds = \sum_M \mu_m(E) \cdot d_m.$$

Furthermore, the absorption value of each layer is decomposed into a path-dependent factor and an energy-dependent factor. The path-dependent factor does not depend on the energy, and the energy-dependent factor does not depend on the path. Hence, the modeling proceeds on the basis of the reformulated absorption equation:

$$I(E) = \int_E I_0(E) \cdot e^{-\Sigma_M \tau_m(E) \delta_m(S)} dE. \quad (2)$$

The energy-dependent factor $\tau_m$ can correspond to the mass attenuation coefficient and the path-dependent factor $\delta_m$ preferably corresponds to the density along the path through the material. In general, $\delta_m$ depends on the path S and is described by $$\delta_m(S) = \int_S \rho_m(r(s)) ds. \quad (3)$$

Since the layers are assumed to be made of homogeneous materials, equation (3) simplifies to $$\delta_m(S) = \rho_m \cdot d_m \quad (4)$$

A next step calculates the unknown path-dependent factors $\delta_m$ of all layers from the absorption X-ray images using the absorption equation (2). The number of unknowns corresponds to the number of assumed layers within the scope of modeling the object. Each absorption X-ray image provides an equation for determining these unknowns; $\tau_m$ and $\rho_m$ are known for the assumed materials. Since the number of equations has to be greater than or equal to the number of unknowns, the number of layers has to be less than or equal to the number of X-ray images. Here, a priori knowledge of the object to be examined can replace one or more X-ray images.

The thicknesses of the layers can be calculated from the path-dependent factors using equation (4). The layers would have these thicknesses if the object to be examined consisted exclusively of the assumed materials. If the object contains other materials than those assumed during the modeling, these other materials result in false contributions to the path-dependent factors and thus to the thicknesses of a plurality of layers. However, as will be shown below, this is unimportant for improving the ability to recognize materials.

In a next method step, at least one synthetic image is calculated from the sum of all layers of the product of the absorption values and the weighting factors. By way of example, the synthesizing equation used during this calculation is $$I_{syn}(E) = \int_E I_0(E) \cdot e^{-\Sigma_M w_m \cdot \tau_m(E) \bar{s}_m(S)} dE \quad (5)$$

Thus, a new image is synthesized from the model of the object, the properties of the assumed materials and the path-dependent factors of the layers. The selection of the weighting factors $w_m$ affords the possibility of designing the synthetic image such that an object including a material to be recognized does not have a contour, or only has a weak contour, in the synthetic image. If all weighting factors are selected to be 1, the synthetic image corresponds to a recorded absorption X-ray image.

The final step includes evaluating the synthetic image. By way of example, the evaluation can be automated, with, for example, an alarm sounding if the object to be examined comprises a material to be recognized. Alternatively or additionally, the evaluation is carried out by displaying the synthetic image on a monitor. Optionally, two or more synthetic images are calculated using different weighting factors and are displayed one after another or next to one another on the monitor. For this, the X-ray inspection system operator switches between the synthetic images using, for example, a button or a switch. In one refinement of the invention, the weighting factors for at least one synthetic image or all synthetic images can be set by the operator.

The absorption value of a layer with a material to be recognized can be weighted using the factor zero during the calculation of the synthetic image. Accordingly, the synthetic image does not contain an absorption component that is associated with the material to be recognized during the modeling of the object. Accordingly, a contour of an object made of the material to be recognized, which contour becomes apparent in the recorded absorption X-ray images, is not contained in the synthetic image. By way of example, the operating staff of the X-ray inspection system deduces the presence of the material to be recognized in the object by the lack of this contour.

In an embodiment of the invention, the weighting factors in the calculation of the synthetic image depend on the position of the pixel in the X-ray image. Accordingly, $w_m = w_m(x,y)$ holds true, with x and y being the coordinates of a pixel in the image. By way of example, this affords the possibility of suppressing the contours of items made of different materials in various regions of the synthetic image using different weighting factors and thus affords the possibility of detecting a plurality of materials to be recognized in a synthetic image.

The absorption caused by a layer during the calculation of the synthetic image is preferably colored as a function of the assumed material of the layer. The coloring is preferably brought about based on the atomic number Z of the material. Thus, for example, metallic materials are colored blue and organic materials are colored orange. This coloring affords simpler detection of the sought after materials by the operating staff of the X-ray inspection system.

An X-ray inspection system according to the invention has means for carrying out the method described above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
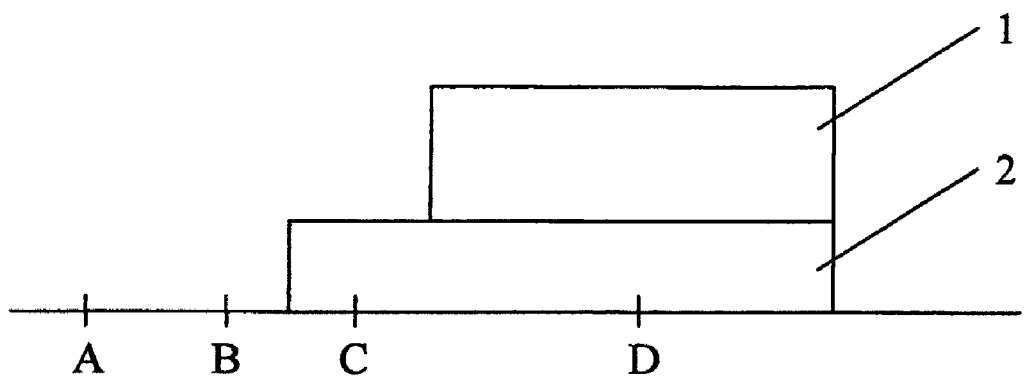
FIG. 1 shows a section through an object to be examined made of two materials.

FIG. 1 illustrates a schematic sectional illustration of an object to be examined that is composed of two materials. Material 1 is the plastic explosive Semtex; material 2 is iron. The thickness of material 1 is 1.5 mm; the thickness of material 2 is 1 mm. Four positions A, B, C and D, where X-ray detectors are arranged, are highlighted in an exemplary fashion. When an absorption X-ray image is recorded, there is no material between the (not illustrated) X-ray source in an X-ray inspection system and the X-ray detectors at positions A and B, there is only material 2 between the X-ray source and the detector at position C and both material 1 and material 2 between the X-ray source and the X-ray detector at position D. The X-ray detectors detect the X-ray radiation emitted by the X-ray source and attenuated by the object.

In a dual-energy X-ray inspection system, two absorption X-ray images of the object are recorded at two different energy spectra of the X-ray radiation. In the present example, the energy $E_L$ of the X-ray radiation in the low-energy recording is between 20 keV and 70 keV; the energy $E_H$ in the high-energy recording is between 70 keV and 140 keV. The absorption X-ray images are two-dimensional images made up of individual pixels, wherein the brightness of each pixel corresponds to the absorptivity of the object to be examined at this image position. The two absorption X-ray images provide both intensities $I(E_L)$ and $I(E_H)$ for each pixel.

Subsequently, the object is modeled mathematically using two layers. In one layer, Semtex is assumed to be material 3; iron is assumed to be material 4 in the other layer. The intensity of the X-ray radiation, which impinges on an X-ray detector after being transmitted through the modeled object, is then calculated from the absorption equation (2) for each pixel. If these theoretical intensities are equated to the measured intensities, this results in the two equations $$I(E_L) = \int_{E_L} I_0(E_L) \cdot e^{-\tau_3(E_L)\cdot\delta_3(S)-\tau_4(E_L)\cdot\delta_4(S)} dE \qquad (6)$$

and $$I(E_H) = \int_{E_H} I_0(E_H) \cdot e^{-\tau_3(E_H)\cdot\delta_3(S)-\tau_4(E_H)\cdot\delta_4(S)} dE \qquad (7)$$

with the two unknowns $\delta_3$ and $\delta_4$. Here, $I_0$ refers to the known intensity of the X-ray radiation that would impinge on a detector if there were no material between X-ray source and detector. $\tau_3$ and $\tau_4$ are known material-specific mass attenuation coefficients, which are independent of the length of the path S of the X-ray radiation through the material but do depend on the energy of the radiation. The densities along the path $\delta_3$ and $\delta_4$ depend on the length of the path S of the X-ray radiation through the material, but are independent of the energy of the radiation.

The two unknowns $\delta_3$ and $\delta_4$ can be calculated using equations (6) and (7). They are connected to the thicknesses of the layers via equations (3) and (4). For illustrative purposes, these thicknesses are used instead of the densities along the path $\delta$ in the figures and the following embodiments.

Figure 2A:
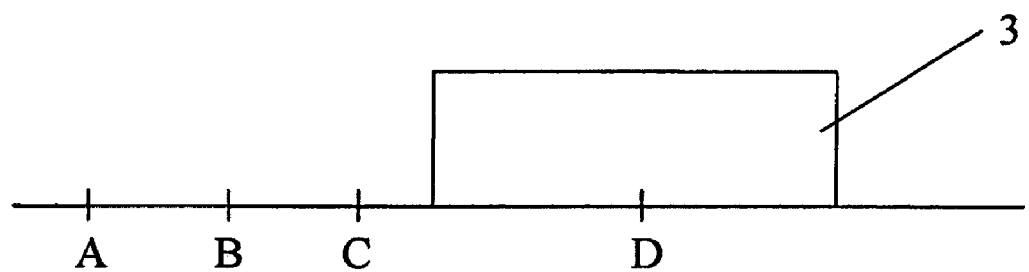
FIG. 2a shows the theoretical absorption thickness of the first assumed material in the object from FIG. 1.
Figure 2B:
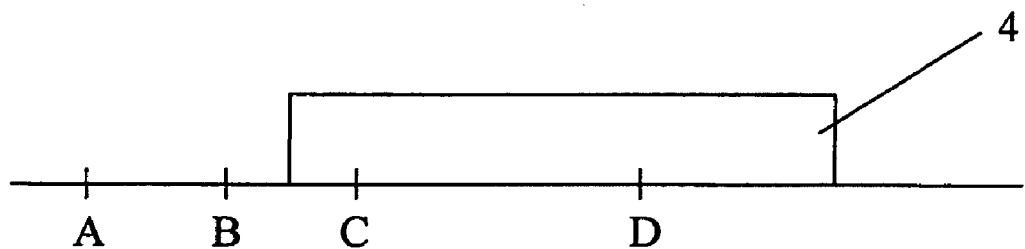
FIG. 2b shows the theoretical absorption thickness of the second assumed material in the object from FIG. 1.

The calculated thickness of material 3 is illustrated in FIG. 2a; the calculated thickness of material 4 is illustrated in FIG. 2b. If, as in the present example, the assumed materials exactly correspond to the materials from which the object is composed, the calculated thicknesses exactly correspond to the actual thicknesses of the materials in the object. If a plurality of items in the object to be examined that are made of the same material are situated in the propagation direction S of the X-ray radiation, these are combined to form a common layer during the modeling of the object. This also holds true if these items are not directly adjacent in the object.

In a next step, at least one synthetic image is calculated using the synthesizing equation (5). Here, it has the following form:

$$I_{syn} = \int_E I_0(E) \cdot e^{-w_3\tau_3(E)\cdot\delta_3(S)-w_4\tau_4(E)\cdot\delta_4(S)} dE$$

The absorption values $\tau_3(E)\cdot\delta_3(S)$ and $\tau_4(E)\cdot\delta_4(S)$ are multiplied by the weighting factors $w_3$ and $w_4$ and summed. Multiplied by the factor −1, the sum forms the exponent of the exponential function in the absorption equation. In the present exemplary embodiment, the weighting factors $w_3$ and $w_4$ are selected to be constant for the entire image, that is to say for all pixels with arbitrary coordinates x and y. The calculated intensities $I_{syn}$ are converted in a known fashion into a two-dimensional image to be displayed on a monitor. Optionally, the components of the individual layers of the overall absorption are colored as a function of the assumed material of the layer.

If the weighting factor $w_4$ is set to equal zero, the synthetic image is based exclusively on the absorption component through the assumed material 3 (Semtex in the present case). FIG. 2a makes it clear that the assumed material 4, which exactly corresponds to the actual material 2, does not provide any image component. A contour, which the material 2 leaves in one of the recorded absorption X-ray images, is missing entirely in the synthetic image. This allows the deduction to be made that the assumed material 4, i.e. iron, is contained within the object. If, by contrast, the weighting factor $w_3$ is set to zero, the synthetic image is based exclusively on the absorption components of the assumed material 4. A contour of the material 1, which contour can be distinguished in an absorption X-ray image, is not contained in the synthetic image, as a result of which it is possible to deduce the presence of the assumed material 3 in the object.

Figure 3:
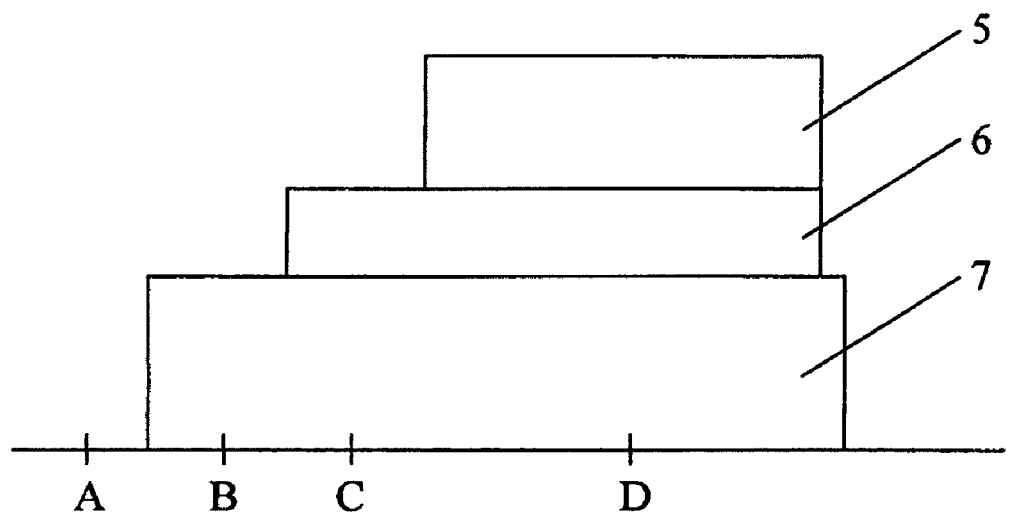
FIG. 3 shows a section through an object with three materials.

FIG. 3 shows a section through an object made of 3 materials. Materials 5 and 6 and the thicknesses thereof correspond to materials 1 and 2 in FIG. 1. Additionally, the object comprises a 2 mm thick material 7. The material 7 is situated in the beam path between the X-ray source and the detectors at positions B, C and D, but not between the X-ray source and the detector at position A.

The object is once again described by a model made of two layers. For this, the equation $$I(E) = \int_E I_0(E) \cdot e^{-\tau_8(E)\cdot\delta_8(S)-\tau_9(E)\cdot\delta_9(S)} dE$$

is used. For this model, material 8 is assumed to be Semtex and material 9 is assumed to be iron, as a result of which these materials correspond to two of the materials actually present in the object. $\delta_8$ and $\delta_9$ are calculated analogously to the first exemplary embodiment.

Since the proposed two-layer model cannot reproduce an object made of three materials correctly, the calculated thicknesses do not correspond to the actual thicknesses of the materials 5 and 6 in the object, even if the materials 8 and 9 are assumed correctly. Rather, the material 7 results in a component in both calculated thicknesses since it does not correspond exactly to any of the assumed materials. This results in the thickness profiles of the material 8 as shown in FIG. 4a and the material 9 as shown in FIG. 4b.

The absorption of the X-ray radiation through the material 7 measured by the X-ray detector at position B corresponds to that absorption that would be caused by 1.2 mm of material 8, i.e. Semtex, and 0.2 mm of material 9, i.e. iron. These mentioned thicknesses form an incorrect offset at positions B, C and D. For Semtex as assumed material 8, which corresponds to the actual material 5, there is an additional, correct thickness component of 1.5 mm at position D and hence there is an overall calculated thickness of 2.7 mm. For the material 9, which was correctly assumed to be the actual material 6 iron, there is an additional thickness component at positions C and D of 1 mm as a result of the object and hence an overall calculated thickness of 1.2 mm.

Figure 4A:
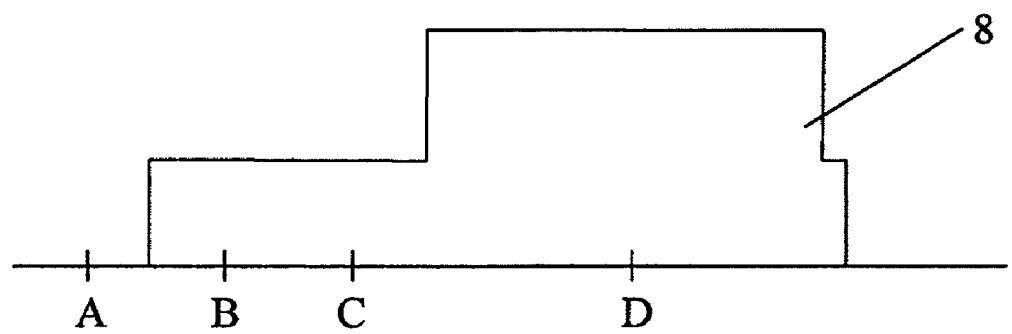
FIG. 4a shows the theoretical absorption thickness of the first assumed material in the object from FIG. 3.
Figure 4B:
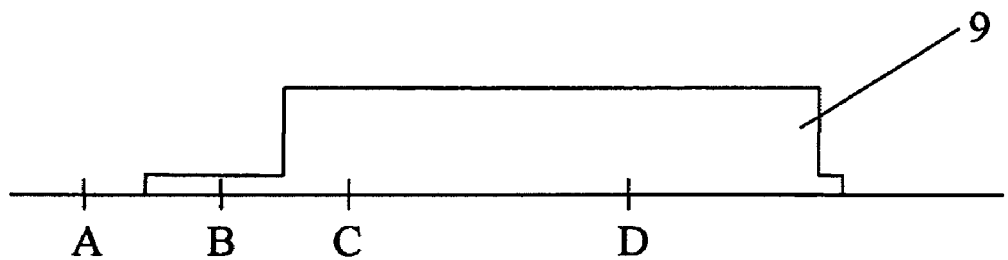
FIG. 4b shows the theoretical absorption thickness of the second assumed material in the object from FIG. 3.

It can be seen from the profiles of the calculated thicknesses in FIGS. 4a and 4b that, although the third material 7 results in an additional component of the thicknesses of the assumed materials, the real contour of an item in the object and having the respective material is still reproduced correctly.

When the weighting factor $w_9$ is selected to be zero, the synthetic image does not contain contours from iron as material 6, although it does contain contours as a result of materials 5 and 7. By contrast, if the weighting factor $w_8$ is selected to equal zero, the synthetic image does not contain any contours caused by Semtex. The lack of a contour compared to a recorded absorption X-ray image can thus allow the presence of the assumed material in the object to be deduced, even if the object contains more or different materials than those taken account of by the mathematical model.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for recognizing materials in an X-ray inspection system, the method comprising:
    irradiating an object to be examined;
    recording at least two absorption X-ray images, of the object to be examined, at different energies;
    mathematically modeling the object by a number of layers assuming a particular material for each layer, wherein an absorption value describes an absorptivity of a layer, the number of layers being less than or equal to the number of X-ray images, and at least one layer being assumed to be a material to be recognized during the inspection;
    decomposing the absorption value of each layer into a path-dependent factor and an energy-dependent factor;
    calculating the path-dependent factors for all layers from the absorption X-ray images using the absorption equation;
    calculating at least one synthetic image from a sum of all layers of the product of the absorption values and selected weighting factors; and
    evaluating the synthetic image.

2. The method as claimed in claim 1, wherein two absorption X-ray images are recorded at two energies.

3. The method as claimed in claim 1, wherein the absorption value of a layer with a material to be recognized is weighted by a factor zero during calculation of the synthetic image.

4. The method as claimed in claim 1, wherein the weighting factors in the calculation of the synthetic image depend on a position of a pixel in the X-ray image.

5. The method as claimed in claim 1, wherein, during calculation of the synthetic image, the absorption caused by a layer is colored as a function of the material assumed for the layer.

6. The method as claimed in claim 1, wherein the energy-dependent factor is a mass attenuation coefficient and the path-dependent factor is a density along the path through the material.

7. The method as claimed in claim 1, wherein the different energies are selected such that an intensity of X-ray radiation transmitted through the object to be examined is reduced.

8. The method as claimed in claim 1, wherein the material of the layers is assumed to be homogeneous.

9. The method as claimed in claim 1, further comprising calculating a thickness of the layers from the path-dependent factors.

10. The method as claimed in claim 1, wherein said calculating at least one synthetic image comprises calculating a plurality of synthetic images using different weighting factors.

11. The method as claimed in claim 1, wherein the different energies comprise a low-energy and a high-energy.

12. The method as claimed in claim 1, wherein the different energies comprise a first energy between 20 keV and 70 keV and a second energy between 70 keV and 140 keV.

13. The method as claimed in claim 1, wherein the absorptive X-ray images are two-dimensional images made up of individual pixels, and
    wherein a brightness of each individual pixel corresponds to the absorptivity of the object to be examined.

14. An X-ray inspection system comprising:
    an X-ray source; and
    a detector configured to detect an x-ray generated by the X-ray source,
    wherein the X-ray inspection system is configured to:
        records at least two absorption X-ray images, of an object to be examined, at different energies;
        mathematically model the object by a number of layers assuming a particular material for each layer, wherein an absorption value describes an absorptivity of a layer, the number of layers being less than or equal to the number of X-ray images, and at least one layer being assumed to be a material to be recognized during the inspection;
        decompose the absorption value of each layer into a path-dependent factor and an energy-dependent factor;
        calculate the path-dependent factors for all layers from the absorption X-ray images using the absorption equation;
        calculate at least one synthetic image from a sum of all layers of the product of the absorption values and selected weighting factors; and
        evaluate the synthetic image.

* * * * *